(12) United States Patent
Ma et al.

(10) Patent No.: US 7,876,025 B2
(45) Date of Patent: Jan. 25, 2011

(54) ULTRASONIC MECHANICAL EMULSIFIER

(75) Inventors: Jan Ma, Singapore (SG); Freddy Y. C. Boey, Singapore (SG); Tock Han Lim, Singapore (SG)

(73) Assignees: Nanyang Technological University, Singapore (SG); Tan Tock Seng Hospital, Singapore (SG)

( * ) Notice: Subject to any disclaimer, the term of this patent is extended or adjusted under 35 U.S.C. 154(b) by 127 days.

(21) Appl. No.: 12/088,221

(22) PCT Filed: Sep. 7, 2006

(86) PCT No.: PCT/SG2006/000260

§ 371 (c)(1),
(2), (4) Date: Aug. 26, 2008

(87) PCT Pub. No.: WO2007/035171

PCT Pub. Date: Mar. 29, 2007

(65) Prior Publication Data

US 2008/0315720 A1    Dec. 25, 2008

(51) Int. Cl.
*H01L 41/08* (2006.01)
(52) U.S. Cl. .................. 310/328; 310/366; 310/369
(58) Field of Classification Search ............ 310/328, 310/366
See application file for complete search history.

(56) References Cited

U.S. PATENT DOCUMENTS

| | | | | |
|---|---|---|---|---|
| 4,038,571 A | * | 7/1977 | Hellenkamp | 310/323.18 |
| 4,785,177 A | * | 11/1988 | Besocke | 250/442.11 |
| 4,841,148 A | * | 6/1989 | Lyding | 850/13 |
| 5,173,605 A | * | 12/1992 | Hayes et al. | 850/1 |
| 5,198,715 A | * | 3/1993 | Elings et al. | 310/328 |
| 5,306,919 A | * | 4/1994 | Elings et al. | 250/442.11 |
| 6,603,239 B1 | * | 8/2003 | Michely et al. | 310/328 |
| 2001/0011176 A1 | | 8/2001 | Boukhny | |
| 2002/0082793 A1 | | 6/2002 | Kadziauskas et al. | |
| 2006/0064081 A1 | | 3/2006 | Rosinko | |

FOREIGN PATENT DOCUMENTS

| | | |
|---|---|---|
| EP | 0 945 732 | 9/1999 |
| JP | 5-95971 | 4/1993 |
| WO | WO 90/03150 | 4/1990 |
| WO | WO 93/13715 | 7/1993 |
| WO | WO 97/45078 | 12/1997 |
| WO | WO 99/15120 | 4/1999 |
| WO | WO 00/00096 | 1/2000 |
| WO | WO 00/30554 | 6/2000 |
| WO | WO 02/05708 | 1/2002 |
| WO | WO 02/07659 | 1/2002 |

* cited by examiner

*Primary Examiner*—Mark Budd
(74) *Attorney, Agent, or Firm*—Dickstein Shapiro LLP

(57) ABSTRACT

A tubular piezoelectric transducer comprising a tube of piezoelectric material and having a plurality of external electrodes for inducing in a first end of the tube at least one movement of a plurality of possible movements; at least two spokes attached to and extending radially inwardly of the tube for movement with the first end; a hub at an inner end of the at least two spokes and being located on the longitudinal axis of the tube, the hub being attached to the at least two spokes for movement therewith; the hub being for receiving therein a probe for movement of the probe with the hub. A phaco-probe incorporating the transducer is also disclosed.

16 Claims, 6 Drawing Sheets

(a)           (b)

ULTRASONIC MECHANICAL EMULSIFIER

FIELD OF THE INVENTION

This invention relates to an ultrasonic mechanical emulsifier and relates more particularly, though not exclusively, to an ultrasonic mechanical emulsifier using piezoelectric material.

REFERENCE TO RELATED APPLICATIONS

Reference is made to our two earlier U.S. patent application Ser. No. 10/611,401 (published as 2004/0118686) filed Jul. 1, 2003 for the invention titled "Piezoelectric Tubes" and Ser. No. 10/611,306 (published as 2005/0017603) filed Jul. 1, 2003 for the invention entitled "Pump" (our "earlier applications"), the contents of which are hereby incorporated by reference as if disclosed herein in their entirety.

BACKGROUND TO THE INVENTION

One of the most important areas in minimally invasive surgery is phacoemulsification surgery, which has revolutionized cataract surgery in the recent years. In phacoemulsification surgery, an ultrasound probe is inserted into the eye. Ultrasound energy is applied to the crystalline lens of the eye to emulsify it. The emulsified material is then removed from the eye using vacuum. The capsular bag is left behind for the implantation of an artificial intraocular lens replacing the cataractous crystalline lens.

Phacoemulsification allows the relatively large cataract to be removed via a small incision. However, the ultrasound energy used may damage the cornea, which is the transparent 'cover' of the eye, causing the loss of the endothelial cell layer. Significant loss of endothelial cells may lead to a later complication known as bullous keratopathy requiring corneal transplant. Bullous keratopathy is now the commonest indication of corneal transplant in many parts of the world.

One of the good surgical techniques which helped to reduce endothelial cell loss is the use of mechanical forces emanating from a phaco probe tip. These forces are better localised than ultrasound energy. Mechanical forces used include techniques known as phaco-chop, and using a second instrument to manually break up small pieces of lens material and the removal of these fragments using high vacuum. The lower the mechanical breaking force, the higher the vacuum force will be required. However, high vacuum has its dangers. It can suck in the posterior capsule thereby rupturing it. Rupture of the posterior capsule can lead to serious complications such as retinal detachment and intraocular lens displacement.

SUMMARY OF THE INVENTION

In accordance with a first preferred aspect there is provided a tubular piezoelectric transducer comprising a tube of piezoelectric material and having a plurality of external electrodes for inducing in a first end of the tube at least one movement of a plurality of possible movements; a hub having its centre located on the longitudinal axis of the tube, the hub being for movement with the first end; the hub being for receiving therein a probe for movement of the probe with the hub.

According to a second preferred aspect there is provided a phaco-probe comprising a tubular piezoelectric transducer including a tube of piezoelectric material and having a plurality of external electrodes for inducing in a first end of the tube at least one movement of a plurality of possible movements; a hub having its centre located on the longitudinal axis of the tube, the hub being for movement with the first end; the hub being for receiving therein a probe for movement of the probe with the hub.

For both aspects the plurality of external electrodes may extend longitudinally of the tube and may be on an external surface of the tube. The plurality of external electrodes may comprise four electrodes arranged as equal quadrants extending longitudinally of the tube. There may be at least two spokes attached to and extending radially inwardly of the tube for movement with the first end. There may be four equally-spaced spokes. The at least two spokes may be at the first end or adjacent the first end. The hub may be of a form selected from: integral with the spokes, formed by the spokes, securely attached to the spokes, formed by the tube, and integral with the tube. The at least two spokes and the hub may be relatively rigid so all motion of the first end is transmitted to the probe through the at least two spokes and hub. The probe may be attachable to the hub by one of: a friction fit, a snap fit, a bayonet fitting, and a screw-thread connection. The plurality of possible movements may be selected from: reciprocating motion of the first end in the direction of the longitudinal axial of the tube, rotational motion of the first end about the longitudinal axis of the tube; vertical oscillation of the first end, horizontal oscillation of the first end; and arcuate oscillation of the first end about the longitudinal axis of the tube. The probe may comprise a head end extending axially outwardly from the first end. The head end may have at its outer end a probe tip.

The probe may be located within a funnel-shaped housing, the tip extending beyond the housing. The funnel-shaped housing and the head end may conduct ultrasonic vibrations able to be produced by the tubular piezoelectric transducer to the probe tip for radiating the ultrasonic vibrations from a phace-probe tip. The phaco-probe tip may comprise a tip of the funnel-shaped housing, and the probe tip. The phaco-probe may further comprise a stack of piezoelectric actuators capable of reciprocal movement in the direction of the longitudinal axis of the tubular piezoelectric transducer. The stack of piezoelectric actuators and the tubular piezoelectric transducer may be able to be operated independently of each other.

BRIEF DESCRIPTION OF THE DRAWINGS

In order than the invention may be fully understood and readily put into practical effect there shall now be described by way of non-limitative example only preferred embodiments of the present invention, the description being with reference to the accompanying illustrative drawings.

In the drawings.

DETAILED DESCRIPTION OF THE PREFERRED EMBODIMENTS

Figure 1:
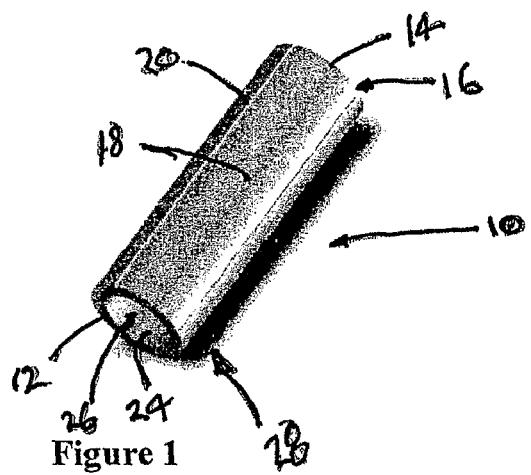
FIG. 1 is a representation of a preferred embodiment of a tubular piezoelectric transducer.

To refer to FIG. 1 there is shown a tubular piezoelectric transducer 10 made of a formulated piezoelectric material and consists of a hollow, radially-poled piezoelectric tube 12 in accordance with our earlier applications. The tube 12 is coated with outer electrodes 14 on its outer curved surface 16 and may have inner electrodes 24 on its inner curved surface 26. The electrode configuration may be varied according to requirements. For example, there may be any number of electrodes: two, three, four, eight, and so forth; or they may extend circumferentially; depending on requirements for each application. For example, in FIG. 1, there are four electrodes 14 on the outer surface in equal, longitudinally-extending quadrants 18 with small gaps 20 between them. The quadrants 18 of the electrodes 14 extend longitudinally of the tube 12.

With this configuration, the transducer 10 is able to perform bending or longitudinal deformations by extension and contraction of that part of the tube 12 having an electrode quadrant 18 to which has been applied an electric field.

The tubular piezoelectric transducer 10 offers a number of advantages: good structural rigidity, easy calibration and high resonant frequency. It can be used in both off-resonance and resonance conditions. The transducer 10 is able to deform in three dimensions, and may do so with a sub-nanometer resolution.

Due to a large mechanical output at resonant frequencies, the use of the transducer 10 at resonant frequencies is of advantage. For the preferred embodiment, the advantage is the ability to combine ultrasonic energy and the induced mechanical energy when the transducer 10 is working at its resonant frequency.

Figure 2:
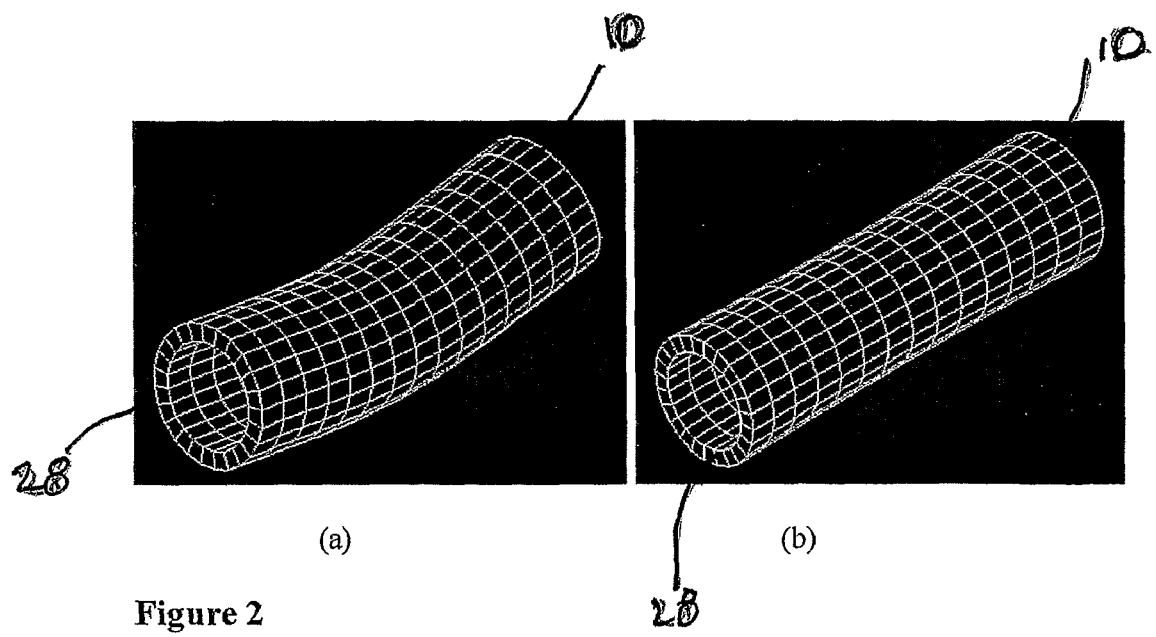
FIG. 2 illustrates the bending and longitudinal deformation of the tubular piezoelectric transducer of FIG. 1 at the resonant frequency with (a) being the bending mode and (b) being the longitudinal mode.
Figure 3:
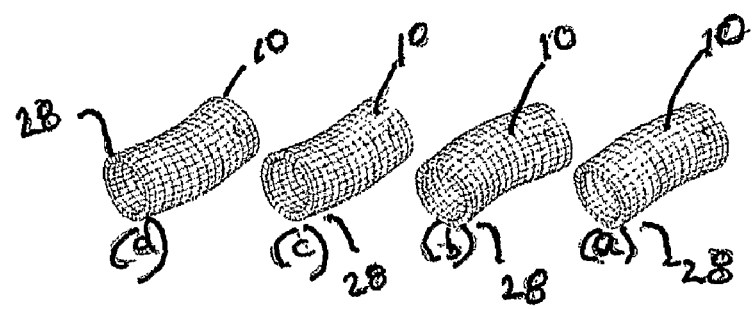
FIG. 3 illustrates the sequential bending of the tubular piezoelectric transducer.

FIGS. 2 and 3 show the bending and longitudinal vibration mode of the transducer 10. The longitudinal vibration or reciprocating motion mode can be obtained by connecting the outer electrodes 14 and applying an electric signal on the outer electrodes 14 and inner electrodes 24 of the transducer 10. The deformation of the transducer 10 reaches its maximum at the resonant frequency of the transducer 10. Due to the large-amplitude harmonic elongation or contraction, an ultrasonic wave will be generated that travels along the longitudinal direction of the transducer 10. The operational frequency may be in the range of KHz to MHz for the transducer 10. The tubular piezoelectric transducer 10 converts electric energy to elastic mechanical vibrations, where the vibration energy generated will then radiate to the processed medium.

Figure 4:
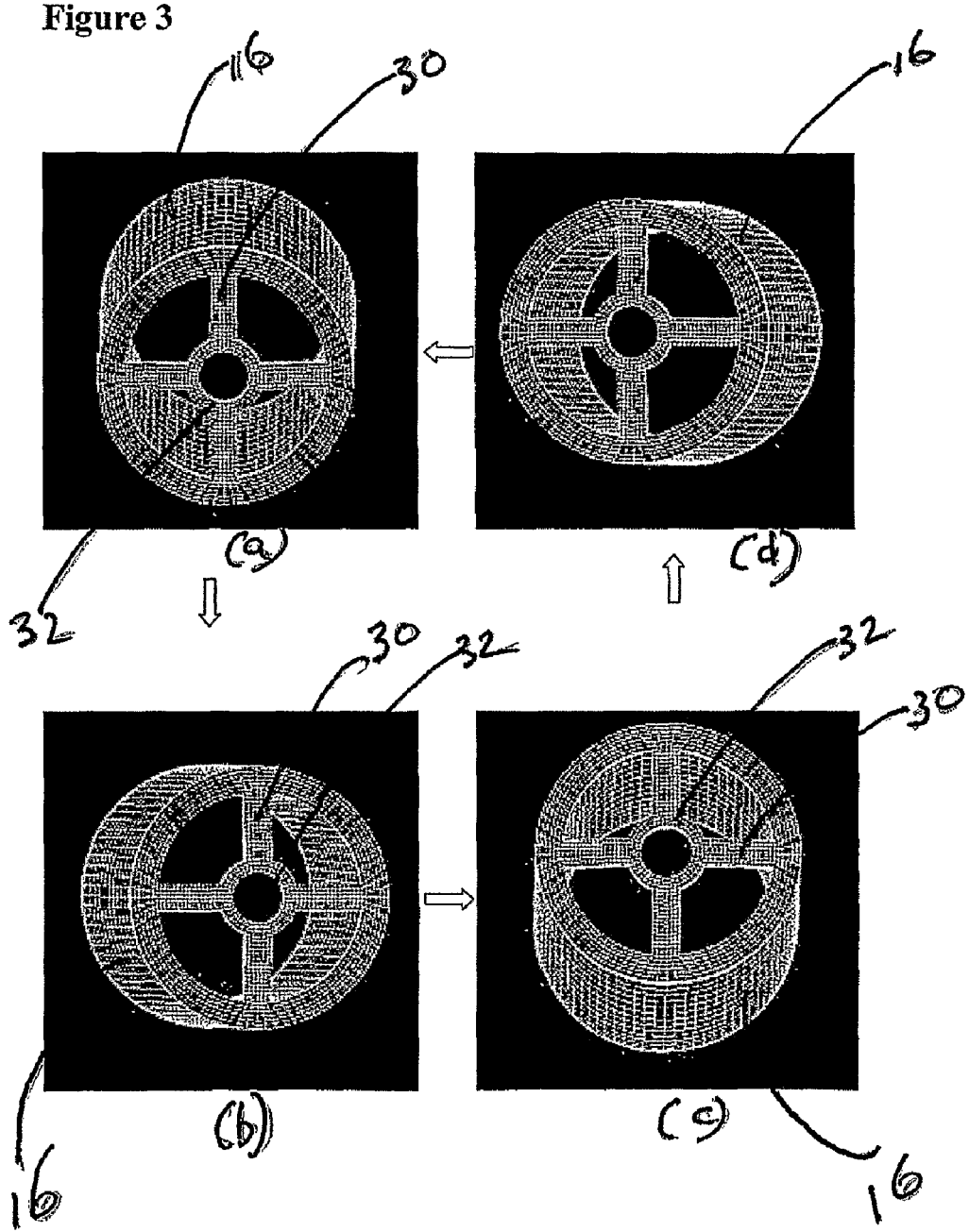
FIG. 4 illustrates the rotational motion of the tubular piezoelectric transducer.

The bending mode is formed by applying an electric field on a pair of diagonally-opposite outer electrodes 14. The bending mode can be sequential and provide twisting and/or rotational actions, as shown in FIG. 3. The motion will be of a first end 28 of the tube 12. If another electric field is applied to the other diagonally-opposite pair of outer electrodes 14, with the electric fields applied to the two pairs of outer electrodes 14 having a phase difference of 90 degrees, a rotational mode can be obtained as seen in FIG. 4. The tubular piezoelectric transducer 10 may rotate clockwise or counter clockwise depending on the excitations of the applied electric fields. As such the rotational motion is a sequential movement as shown in FIGS. 3 and 4:

(a) in FIGS. 3(a) and 4(a), the first end 28 of the transducer 10 is bent downwardly;

(b) in FIGS. 3(b) and 4(b) the first end 28 of the transducer 10 is bent sideways to the right;

(c) in FIGS. 3(c) and 4(c) the first end 28 of the transducer 10 is bent upwardly; and (d) in FIGS. 3(d) and 4(d) the first end 28 of the transducer 10 is bent sideways to the left.

By following this sequence, an anti-clockwise rotational movement of the first end 28 is obtained. Other combinations of movements may be used. For example, a sequential combination of (a) and (c) will provide a vertical oscillation; a sequential combination of (b) and (d) will provide a horizontal oscillation; a sequential combination of (a) with (b) and/or (d) will provide an lower arcuate oscillation; a sequential combination of (c) with (b) and/or (d) will provide an upper arcuate oscillation; a sequential combination of (d) with (a) and/or (c) will provide a left-hand arcuate oscillation; and a sequential combination of (b) with (a) and/or (c) will provide a right-hand arcuate oscillation.

As such the motions may any one of, or any combination of two or more of:

reciprocating motion in the direction of the longitudinal axial of the tube 12;

rotational motion about the longitudinal axis of the tube 12;

vertical oscillation;

horizontal oscillation; and arcuate oscillation.

To assist the output of the rotational motion of the first end 28, the transducer 10 may have radially-directed spokes 30 and a central hub 32 at or adjacent the first end 28. The spokes 30 and hub 32 may be integral with the tube 12, or may be formed separately and subsequently attached to the tube 12. The number of spokes 30 may be as required or desired. As shown there are four spokes 30. It has been found that if there are four outer electrodes 14 a relatively smooth rotational movement can be achieved. However, there is no direct relationship between the number of electrodes 14 and the number of spokes 30. The hub 32 may be integral with the spokes 30, be formed by the spokes 30, or be securely attached to the spokes 30. The spokes 30 and hub 32 may be of any suitable material, including a non-piezoelectric material. The centre of the hub 32 is located on the central, longitudinal axis of the tube 12. The spokes 30 and the hub 32 are preferably relatively rigid so all motion of the first end 28 is transmitted to an object through the spokes 30 and/or hub 32.

The rotational motion is a functional motion of the transducer 10. Due to this motion, an object that engages the hub 32 will be forced to move with the hub 32 due to the frictional interaction at the contact area within the hub 32. This allows the transducer 10 to be a larger piezo-tube, and the working motion be induced via the radially-directed spokes 30 and the central hub 32.

The tube 12 may be produced by an extrusion process, and the spokes 30 and hub 32 added subsequently. Alternatively, the tube 12, spokes 30 and hub 32 may be integrally formed.

When the applied electric fields to the electrodes 14, 24 are synchronized, the extension and contraction of the transducer 10 is in the direction of the longitudinal axis of the tube 12. This provides a linear motion. It also provides a second mode of mechanical force, and will enable the emission of ultrasonic energy at a designed focus point when at the resonant frequency.

In this embodiment, a probe 40 is connected to the tubular piezoelectric transducer 10 either directly or by the spokes 30 and hub 32. The probe 40 has two main functions: to provide a small tip for micro-surgical procedures, and to focus and amplify the vibration energy. The probe 40 concentrates the vibration energy at its tip, and radiates the resultant ultrasonic energy in a focused manner. The length of the probe 40 depends on the frequency applied. For example, the optimal length is inversely proportional to the frequency of operation of the tubular piezoelectric transducer 10.

Figure 5:
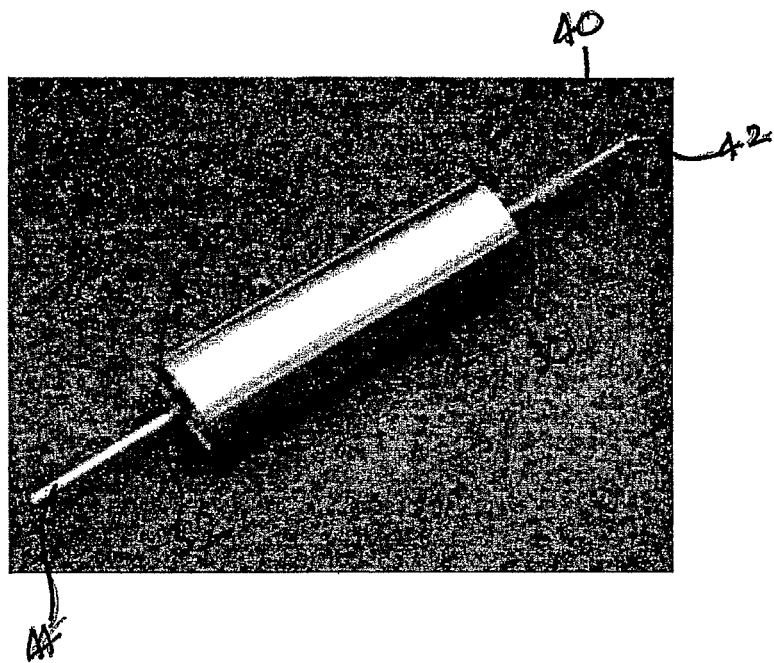
FIG. 5 is a perspective view of the tubular piezoelectric transducer with probe fitted.

FIG. 5 shows the transducer 10 with the probe 40 attached thereto by engagement with the hub 32. The probe 40 may pass through the transducer 10 from the first end. The probe has a head end 42 extending axially outwardly from the first end 28. Extending axially outwardly from the rear end 34 of the tube 12 is a rear sleeve 44. Rear sleeve 44 may pass to the transducer 10. The attachment of the probe 40, or the head end 42 of the probe 40, to the hub 32 may be: a friction fit; a snap fit; use a bayonet fitting; a screw-thread connection; or otherwise as required or desired. Power supply for the electrodes 14 may be through the rear sleeve 44.

Figure 6:
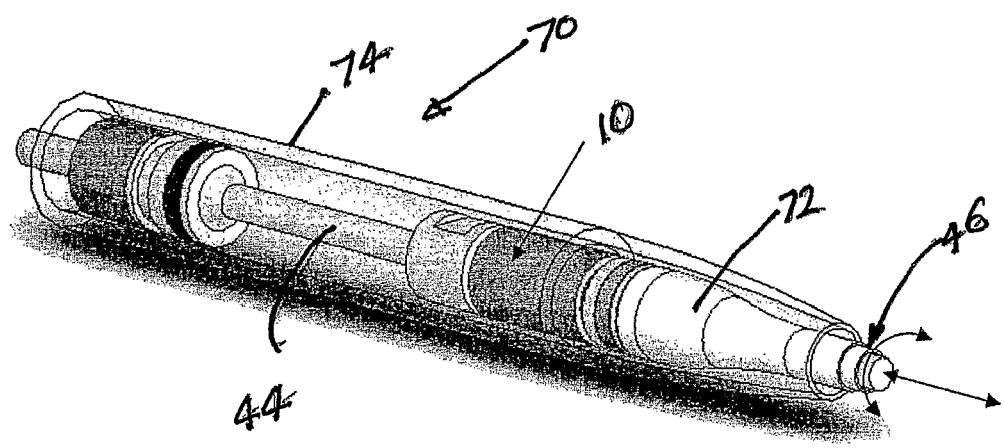
FIG. 6 shows an assembled phaco-probe with the tubular piezoelectric transducer.
Figure 7:
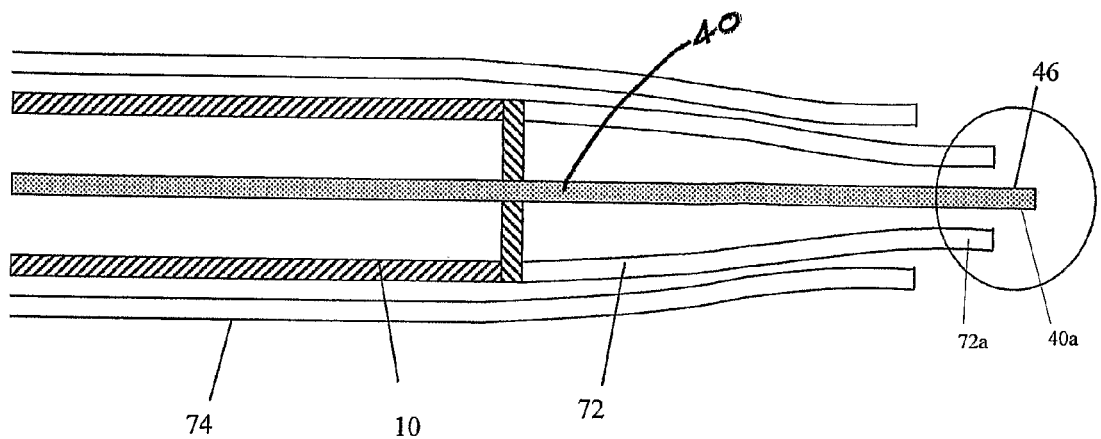
FIG. 7 is a partial longitudinal, vertical cross-sectional view of the phaco-probe of FIG. 6.

FIGS. 6 and 7 show a phaco probe 70 of standard and known construction to which a tubular piezoelectric transducer 10 has been fitted. The tubular piezoelectric transducer 10 includes the probe 40 the head end 42 of the probe 40 being located in a funnel-shaped housing 72. The phaco probe 70 has a tip 46. The tip 46 comprises the tip 72a of the housing 72 and the tip 40a of the probe 40. The tip 42a extends from the head end 42 and may be a separate component, or may be integral with the head end 42. The entire assembly (apart from the tip 46 and part of the rear sleeve 44) is contained within a housing body 74. The tip 46 is capable of the various movements described above. The housing 72 and the head end 42 of probe 40 conduct the ultrasonic vibration energy produced by the tubular piezoelectric transducer 10 to the tip 46 so that the ultrasonic vibration generated by the tubular piezoelectric transducer 10 radiates outwardly from the tip 46.

The housing 72 is connected to the tubular piezoelectric transducer 10 such that the longitudinal motion translates to the tip 72a of the housing 72. The main function of the tip 46 is to concentrate and radiate the ultrasonic energy as well as providing the rotational, vertical and horizontal motion.

Figure 8:
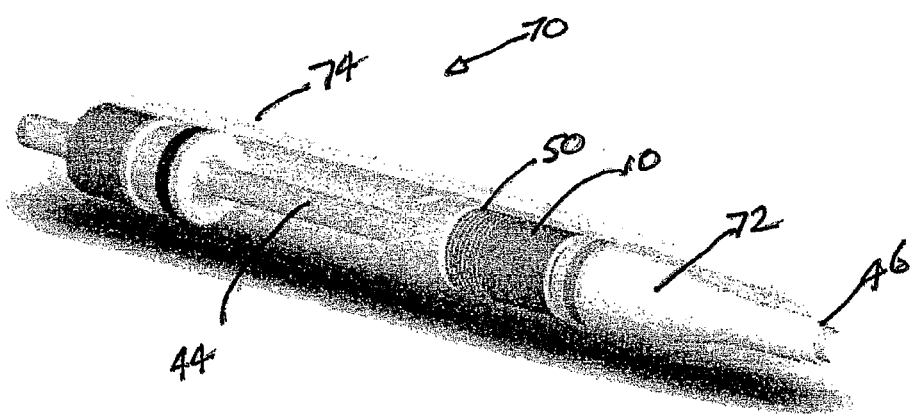
FIG. 8 shows the phaco-probe of FIG. 6 with PZT stacks.
Figure 9:
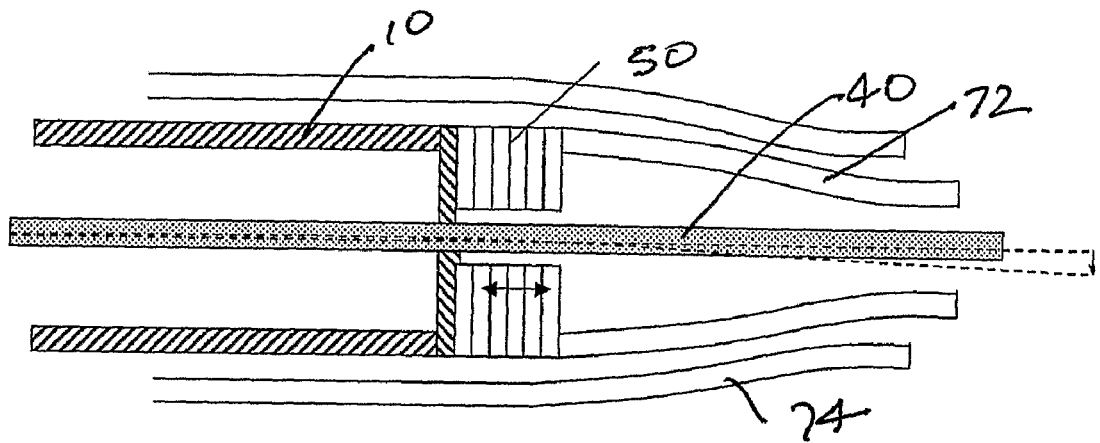
FIG. 9 is a partial longitudinal, vertical cross-sectional view of a first variant of the phaco-probe of FIG. 8.
Figure 10:
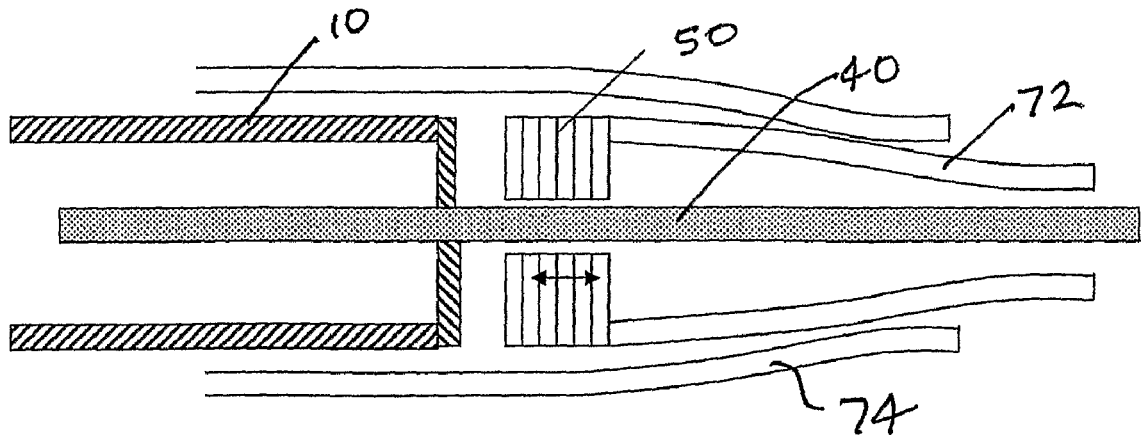
FIG. 10 is a partial longitudinal, vertical cross-sectional view of a second variant of the phaco-probe of FIG. 8.
Figure 11:
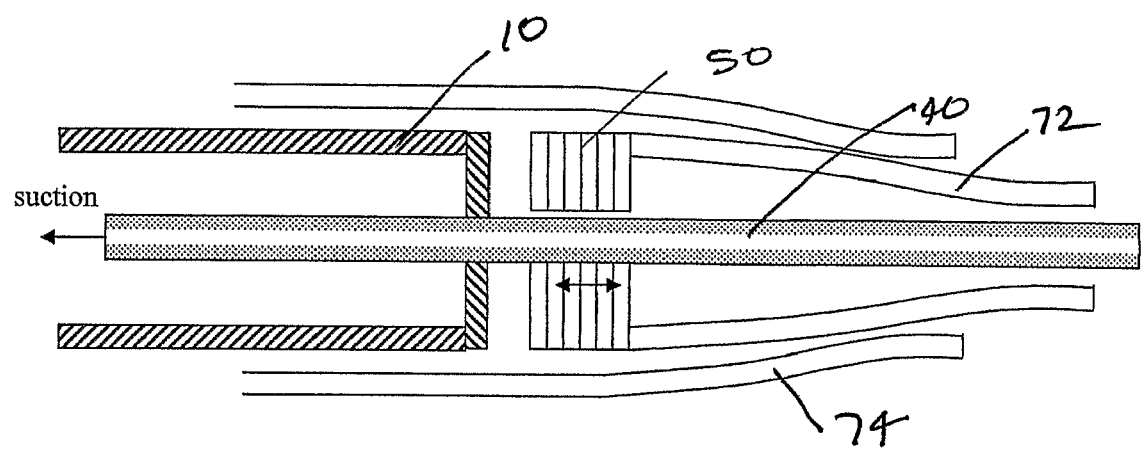
FIG. 11 is a partial longitudinal, vertical cross-sectional view of a variant of the phaco-probe of FIG. 10.

As shown in FIGS. 9 to 11, the tubular piezoelectric transducer 10 can be combined with a stack 50 of piezoelectric actuators of known design and construction and only being capable of reciprocal movement in the direction of the longitudinal axis of the stack 50 and/or tubular piezoelectric transducer 10. The combination of the tubular piezoelectric transducer 10 with the PZT stack may be in any one or more of various configurations. The stack 50 can be located and connected in series at either end of the tubular piezoelectric transducer 10. The first configuration of FIG. 8 has the stack 50 at the end of the tubular piezoelectric transducer 10 remote from the tip 46. As shown in FIGS. 9 and 10, the stack 50 is at the end of the tubular piezoelectric transducer 10 adjacent the tip 46. In FIG. 9 the stack 50 is attached to the end of the tubular piezoelectric transducer 10 whereas in FIG. 10 the stack 50 is apart from the end of the tubular piezoelectric transducer 10. The stack 50 may be able to be operated independently of the tubular piezoelectric transducer 10, and the tubular piezoelectric transducer 10 may be able to be operated independently of the stack 50, to allow a surgeon to have more control over the extent of the motion.

The function of the PZT stack 50 is to increase the magnitude of the longitudinal motion of the housing 72. The tip 72a of the housing 72 provides most of the longitudinal mechanical motion. The magnitude of the longitudinal motion is the combination of the longitudinal motion of the tubular piezoelectric transducer 10 and the PZT stack 50. The housing 72 will transmit the ultrasonic energy from the PZT stack 50 and the tubular piezoelectric transducer 10.

The tip 40a of the probe 40 also transmits ultrasonic energy. In addition, the tubular piezoelectric transducer 10 enables the rotational, vertical and horizontal motion of the probe 40 that is amplified at the tip 46 due to the length of the probe 40.

As shown in FIG. 11, the probe 40 may be hollow such that one end is connected to a vacuum suction pump. In this way, the broken lens can be extracted from the eye.

Figure 12:
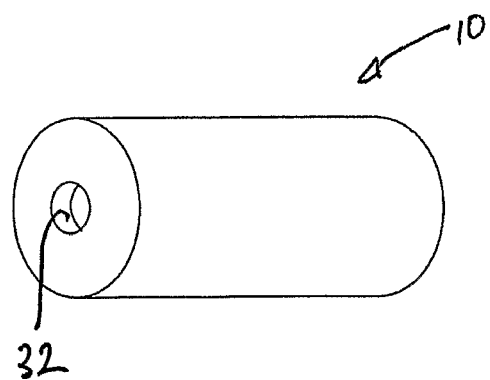
FIG. 12 is an illustration of an alternative form of the tubular piezoelectric transducer.

In FIG. 12 the tubular piezoelectric transducer 10 is solid at least at the first end 28 and forms the hub 30 so there is no need for spokes 30 where the piezoelectric transducer is solid. This is at the first end 28 as illustrated. The hub 30 is formed by and/or is integral with the tube 12.

The performance of the transducer 10 may be adjusted over a wide range. Rotational speeds of up to 8,000 rpm have been achieved with up to 10 mNm of torque. Less than 1 W output power was required.

The embodiments described include a device that is able to provide mechanical energy coupled with ultrasonic energy for the emulsification function. The micro actuator uses a tubular piezoelectric transducer that provides a mechanical force to a probe to enable the probe to break the lens into small pieces, where the driven tip will provide faster disrupting force than manual chopping forces. It will also provide a more controlled and contained force delivery compared to an ultrasonic or laser phaco-tip, leading to safer surgery with improved results. Most importantly, the actuation combines mechanical and ultrasonic functions into one micro-surgical tool. This allows a minimal incision, and interruption, for the cataract procedure.

The apparatus may also be used for other medical and non-medical applications such as, for example:
  (a) dissolving or disintegrating of foreign deposits of material from vessels including cholesterol in blood vessels, and blood clots;
  (b) dissolving or disintegrating materials; or
  (c) micro-positioning.

Whilst there has been described in the foregoing description preferred embodiments of the present invention, it will be understood by those skilled in the technology concerned that many variations in details of design, construction and/or operation may be made without departing from the present invention.

The invention claimed is:

1. A phaco-probe comprising a tubular piezoelectric transducer including a tube of piezoelectric material and having a plurality of external electrodes for inducing in a first end of the tube at least one movement of a plurality of possible movements; a hub having its centre located on the longitudinal axis of the tube, the hub being for movement with the first end; the hub being for receiving therein a probe for movement of the probe with the hub; wherein movement of the probe comprises controllable localized mechanical vibrations for disintegrating a lens in an eye; and wherein there are at least two spokes attached to and extending radially inwardly of the tube for movement with the first end, the hub being at an inner end of the at least two spokes.

2. A phaco-probe as claimed in claim 1, wherein the plurality of external electrodes extend longitudinally of the tube.

3. A phaco-probe as claimed in claim 1, wherein the plurality of external electrodes are on an external surface of the tube.

4. A phaco-probe as claimed in claim 1, wherein the plurality of external electrodes comprise four electrodes arranged as equal quadrants extending longitudinally of the tube.

5. A phaco-probe as claimed in claim 1, wherein the at least two spokes are at a location selected from the group consisting of: at the first end, and adjacent the first end.

6. A phaco-probe as claimed in claim 1, wherein the hub is of a form selected from the group consisting of: integral with the spokes, formed by the spokes, securely attached to the spokes, formed by the tube, and integral with the tube.

7. A phaco-probe as claimed in claim 1, wherein the at least two spokes and the hub are relatively rigid so all motion of the first end is transmitted to the probe through the at least two spokes and hub.

8. A phaco-probe as claimed in claim 1, wherein the probe is attachable to the hub by one selected from the group consisting of: a friction fit, a snap fit, a bayonet fitting, and a screw-thread connection.

9. A phaco-probe as claimed in claim 1, wherein the plurality of possible movements are selected from the group consisting of: reciprocating motion of the first end in the direction of the longitudinal axial of the tube, rotational motion of the first end about the longitudinal axis of the tube; vertical oscillation of the first end, horizontal oscillation of the first end; and arcuate oscillation of the first end about the longitudinal axis of the tube.

10. A phaco-probe as claimed in claim 1, wherein the probe extends axially outwardly from the first end and has at its outer end a probe tip.

11. A phaco-probe as claimed in claim 10, wherein the probe is located within a funnel-shaped housing, the probe tip extending beyond the funnel-shaped housing.

12. A phaco-probe as claimed in claim 11, wherein the funnel-shaped housing and the head end conduct the ultrasonic vibrations to the probe tip for radiating the ultrasonic vibrations from a phaco-probe tip.

13. A phaco-probe as claimed in claim 1 further comprising a stack of piezoelectric actuators capable of reciprocal movement in the direction of the longitudinal axis of the tubular piezoelectric transducer.

14. A phaco-probe as claimed in claim 13, wherein the stack of piezoelectric actuators and the tubular piezoelectric transducer are able to be operated independently of each other.

15. A phaco-probe as claimed in claim 12, wherein the phaco-probe tip comprises a tip of the funnel-shaped housing, and the probe tip.

16. A phaco-probe as claimed in claim 1, wherein the probe is hollow for extraction of the disintegrated lens from the eye by connection of one end of the probe to a vacuum suction pump.

* * * * *